(12) United States Patent
Puneet

(10) Patent No.: US 7,596,827 B1
(45) Date of Patent: Oct. 6, 2009

(54) TOOTHBRUSH WITH INDICATOR OF USE

(75) Inventor: Nanda Puneet, Cerritos, CA (US)

(73) Assignee: Dr. Fresh, Inc., Buena Park, CA (US)

( * ) Notice: Subject to any disclaimer, the term of this patent is extended or adjusted under 35 U.S.C. 154(b) by 638 days.

(21) Appl. No.: 10/985,231

(22) Filed: Nov. 10, 2004

(51) Int. Cl.
*A61C 17/22* (2006.01)
*A46B 9/04* (2006.01)

(52) U.S. Cl. .......................... 15/22.1; 15/105; 15/167.1

(58) Field of Classification Search ............... 15/22.1, 15/105, 167.1
See application file for complete search history.

(56) References Cited

U.S. PATENT DOCUMENTS

| | | | |
|---|---|---|---|
| 5,485,646 A | 1/1996 | Merritt | |
| 5,561,881 A * | 10/1996 | Klinger et al. | ............... 15/22.1 |
| 5,572,762 A * | 11/1996 | Scheiner | ..................... 15/105 |
| 5,801,637 A | 9/1998 | Lomholt | |
| 6,029,303 A | 2/2000 | Dewan | |
| 6,106,294 A | 8/2000 | Daniel | |
| 6,389,633 B1 | 5/2002 | Rosen | |
| 6,536,068 B1 | 3/2003 | Yang et al. | |
| 6,606,755 B1 | 8/2003 | Robinson et al. | |
| 6,611,780 B2 * | 8/2003 | Lundell et al. | ............... 702/122 |
| 6,735,802 B1 * | 5/2004 | Lundell et al. | ............... 15/22.1 |
| 6,954,961 B2 * | 10/2005 | Ferber et al. | ................. 15/22.1 |
| 7,013,522 B2 * | 3/2006 | Kumagai | ..................... 15/105 |
| 2006/0037158 A1 * | 2/2006 | Foley et al. | ................... 15/105 |

FOREIGN PATENT DOCUMENTS

| | | |
|---|---|---|
| DE | 004029770 A1 | 3/1992 |
| FR | 002724297 A1 | 3/1996 |

* cited by examiner

*Primary Examiner*—Randall Chin
(74) *Attorney, Agent, or Firm*—McKee, Voorhees & Sease, P.L.C.

(57) ABSTRACT

The present invention relates to a toothbrush providing an indication of use, including a toothbrush body having a first end and an opposite second end adapted for receiving a head containing bristles, a control circuit disposed within the toothbrush body, the control circuit adapted for counting a number of uses of the toothbrush; and a display electrically connected to the control circuit, the display adapted for displaying the number of uses of the toothbrush.

4 Claims, 3 Drawing Sheets

TOOTHBRUSH WITH INDICATOR OF USE

BACKGROUND OF THE INVENTION

The present invention relates to a toothbrush providing an indication of use, and a method of toothbrush use. In the design and use of a toothbrush, there is a need for an indication to inform the user that a new head is needed. Therefore, the primary objective of the present invention is to provide a display adapted for displaying the number of uses of the toothbrush. In the design and use of a toothbrush, there is a need for a clock. Therefore, a further objective of the present invention is to provide a clock within the toothbrush body. A still further objective of the present invention is to provide a device which is easy to use and economical to manufacture. The means and method of accomplishing these and other objectives will become apparent from the following description of the invention.

SUMMARY OF THE INVENTION

The foregoing objectives may be achieved by a toothbrush having a first end and an opposite second end adapted for receiving a head containing bristles; a control circuit disposed within the toothbrush body, the control circuit adapted for counting a number of uses of the toothbrush; a display electrically connected to the control circuit, the display adapted for displaying the number of uses of the toothbrush, and a clock display electrically connected to the control circuit, the clock display adapted for displaying the time of day.

DETAILED DESCRIPTION OF THE PREFERRED EMBODIMENT

Figure 1:
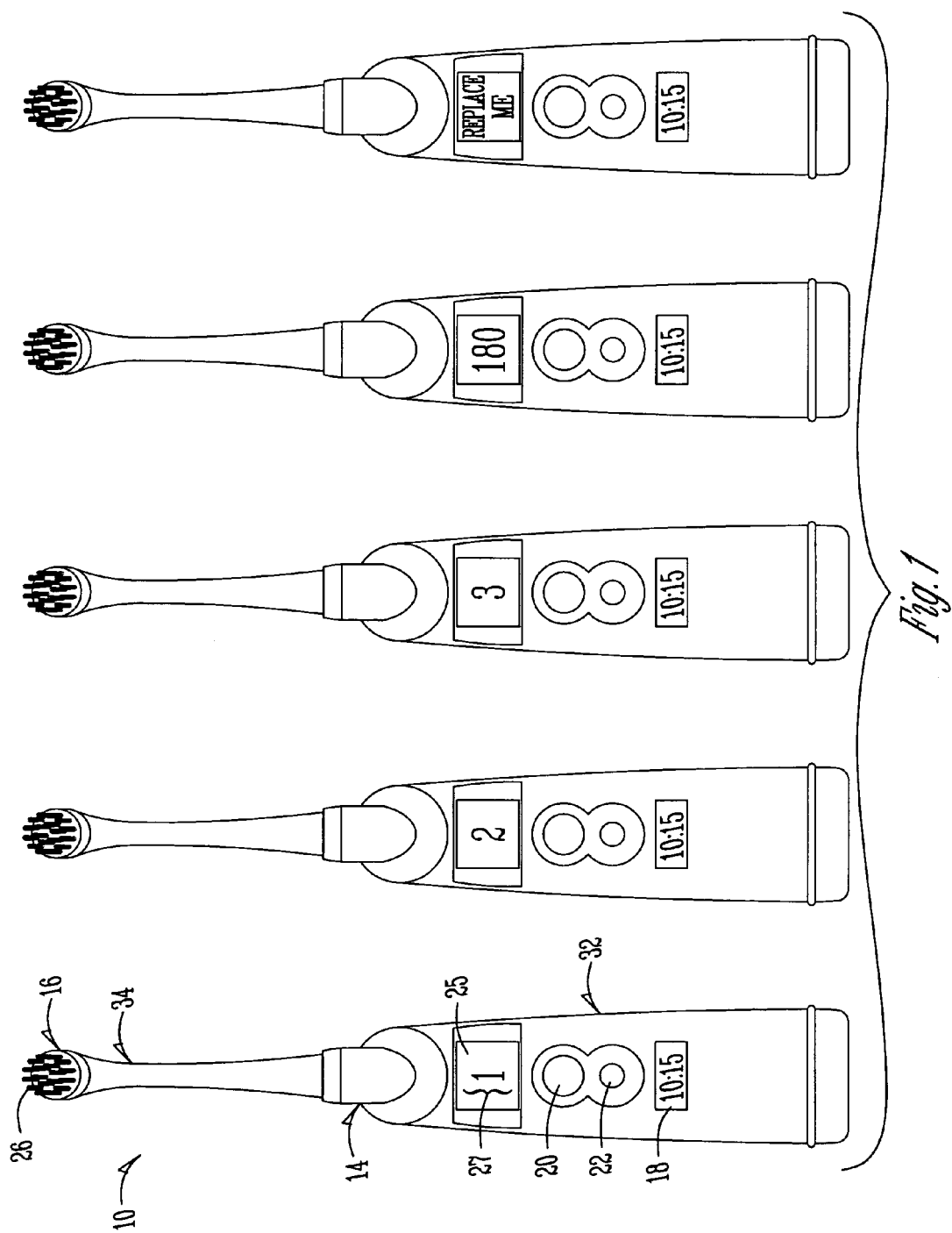
FIG. 1 is a front view of five toothbrushes with clock display displaying the time of day and the other display displaying the number of uses of the toothbrush or a message to replace the head.

Referring to FIG. 1, 10 generally refers to the toothbrush of the present invention that comprises a toothbrush body 14 having a first end 32 and an opposite second end 34 adapted for receiving a head 16 containing bristles 26.

The first end 32 of the toothbrush body is where the toothbrush 10 is gripped and includes a clock display 18 and an on button 20 and off button 22 used to control the action of the head 16. The first end 32 also includes a display 25 containing a message 27 that advances one digit every time the toothbrush 10 is turned off with the off button 22. Alternatively, the message 27 advances one digit every time the toothbrush 10 is turned on with the on button 20. Also, the toothbrush 10 can be turned on and off with a single toggle switch (not shown) with the message 27 advancing one digit every on-off cycle. In the preferred embodiment the display 25 displays the number of times the toothbrush 10 is used. If the toothbrush 10 is used twice daily for 90 days, the message 27 would read "180". After that, rather than advancing one digit, the message 27 would read "replace me" instructing the user to replace the head 16. In other embodiments, the "replace me" message 27 appears after 90 or 360 or any other number of uses that corresponds to the lifetime of the head 16. Preferably, the body 14 contains a cavity to fit a battery. The clock display 18 and the display 25 may be liquid crystal or light emitting diode displays. Although it is preferred that the toothbrush quantifies use by number of uses, the present invention contemplates other variations in quantifying use.

Figure 2:
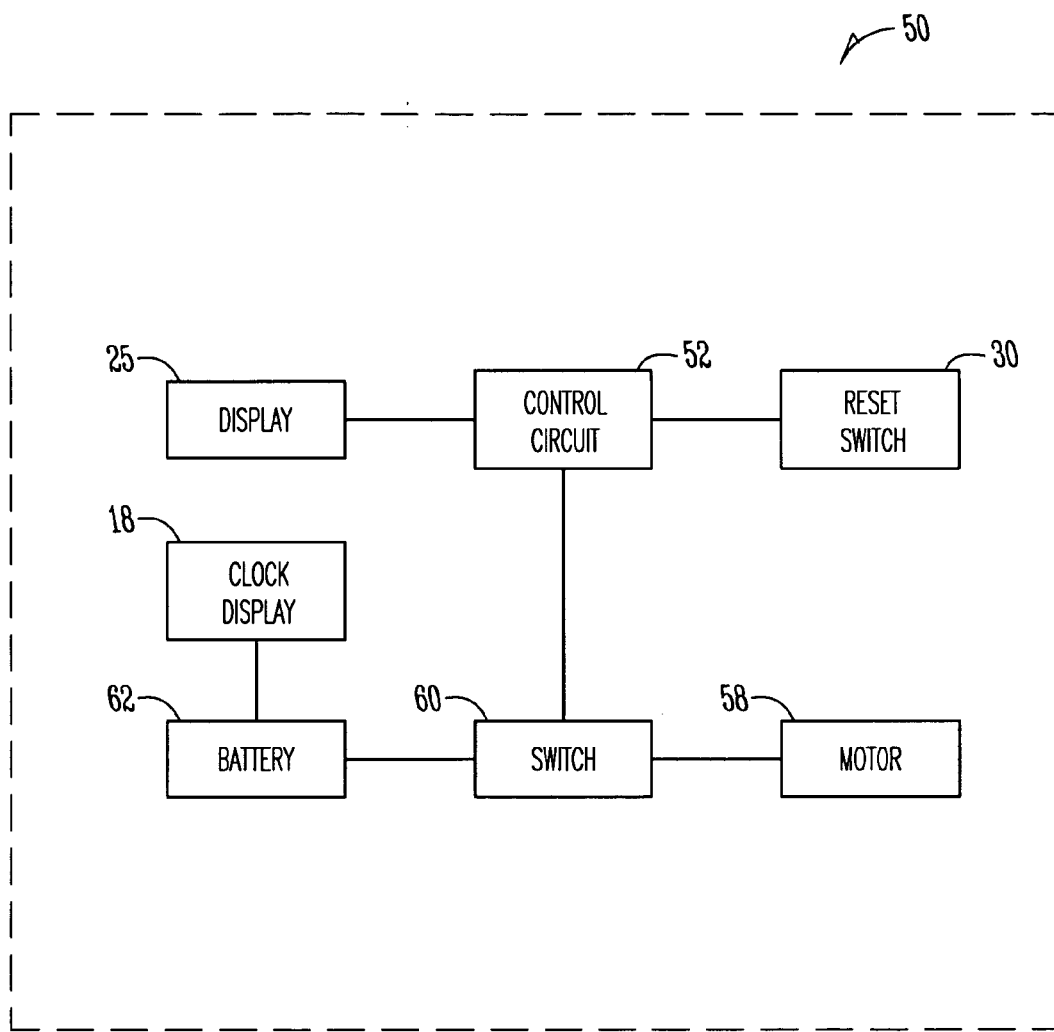
FIG. 2 is a block diagram showing an electrical schematic of the present invention.

FIG. 2 provides a block diagram showing the electric schematic of the present invention. The system 50 includes a control circuit 52. The present invention contemplates that the control circuit 52 can include an intelligent control such as a processor, a microcontroller, or other intelligent control. The control circuit 52 is electrically connected to the display 25, the reset switch 30 and the switch 60. The control circuit 52 controls the display 25 which displays a message 27 (not shown) showing the number of times the toothbrush 10 has been used. The reset switch 30 is used to reset the message 27 on the display 25 to "0" when a new head 16 is attached to the toothbrush 10. The reset switch 30 resets a count within the control circuit 52 to "0."

A motor 58 used to drive the toothbrush 10 is electrically connected to a switch 60. The switch can include one or more buttons such as the on 20 and off 22 buttons (not shown) to turn on and off the motor 58 to drive the toothbrush 10. The switch is electrically connected to a battery 62 and the control circuit 52. The battery 62 is also electrically connected to other electrical components within the device, including the control circuit 52, the display 25 and the clock display 18. In addition, the present invention contemplates that various power conditioning circuits can be used as necessary to provide proper current to the various electronic devices.

Figure 3:
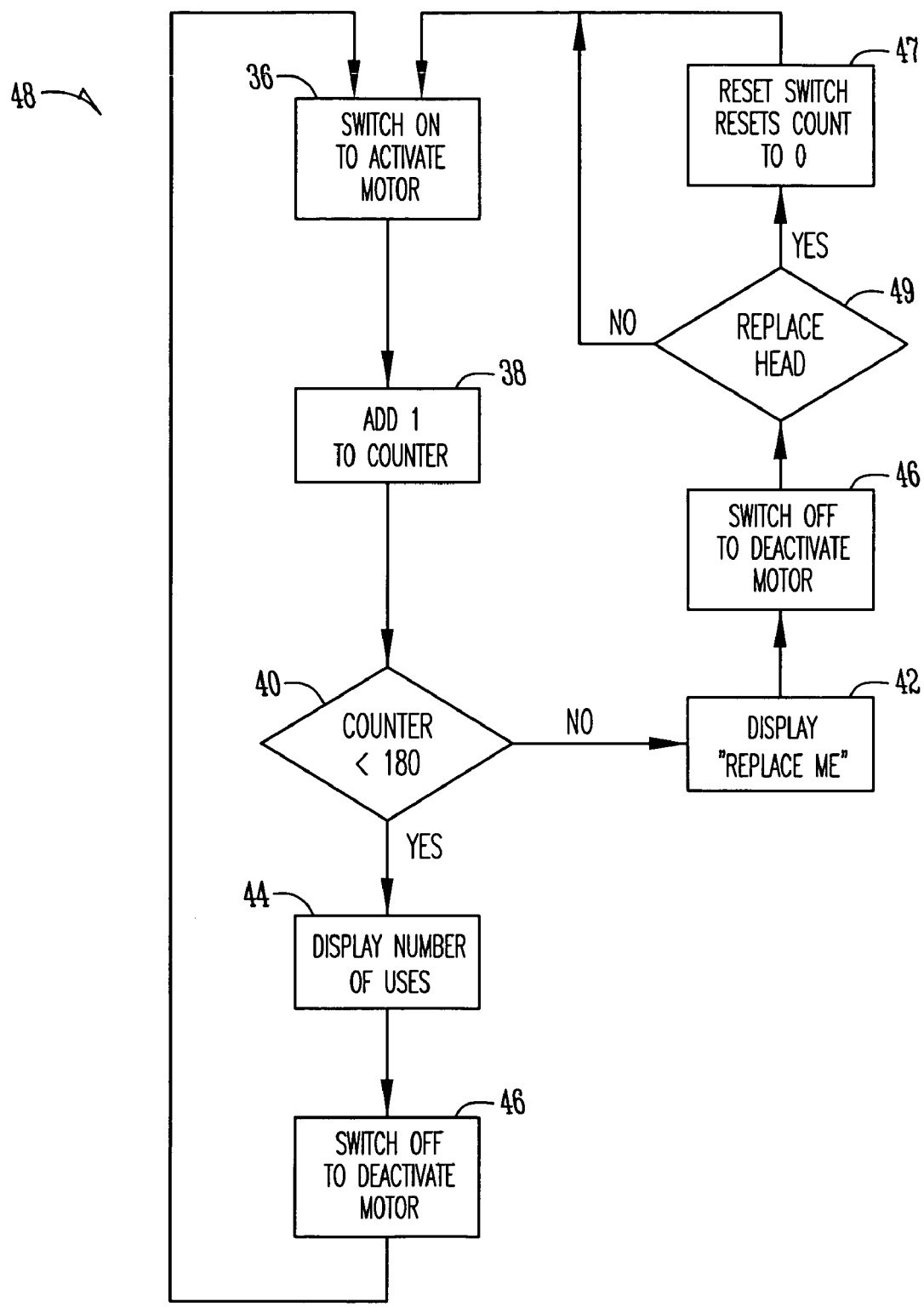
FIG. 3 is a flow chart that shows how the counting, a measure of use, is performed.

FIG. 3 is a flow diagram 48 that shows how the counting, a measure of use, is performed. First, the toothbrush 10 is switched on to activate the motor 36. 1 is added to the counter 38. If the counter 40 is <"180", the number of uses is displayed 44 and, after the use, the toothbrush 10 is switched off, deactivating the motor 46. The process begins anew when the motor is switched on 36. If the counter 40 is ≧"180", the display 25 reads "replace me" 42. If the head 16 is replaced 49 after switching off the motor 46, the reset switch will reset the switch count 47 to "0". If the head 16 is not replaced 49, the display 25 will continue to read "replace me". The process begins anew when the motor is switched on 36.

In the drawings and specifications there has been set forth a preferred embodiment of the invention, and although specific terms are employed, their use is in a generic descriptive sense only and not for purposes of limitation. Changes in the form and the proportion of parts as well as in the substitution of equivalents are contemplated as circumstance may suggest or render expedient without departing from the spirit or scope of the invention in the following claims. For example, the present invention contemplates variations in the power source, the type of indication of use, whether a clock is included, and other variations in structure and function.

What is claimed is:

1. A toothbrush providing an indication of use, comprising:
   a toothbrush body having a first end, an opposite second end, an inside, and an outside;
   a head connectable to the body and containing bristles thereon;
   a control circuit disposed on the inside of the toothbrush body, the control circuit providing a count of the number of uses of the toothbrush;
   a switch electrically connected to the control circuit and being movable between an on position which is actuated and an off position which is de-actuated;
   the control circuit providing a count of the number of uses of the toothbrush by the number of on positions or the number of off positions;

a first display electrically connected to the control circuit displaying a digit that shows the number of uses of the toothbrush, the first display being visible from the outside of the toothbrush body;

a motor connected to the head for driving the head and electrically connected to the switch for being actuated for moving the bristles when the switch is in the on position and being de-actuated for not moving the bristles when the switch is in the off position.

2. The toothbrush of claim 1 wherein the first display shows after a predetermined number of uses a message indicating that the head requires replacement.

3. A toothbrush providing an indication of use, comprising:

a toothbrush body having a first end, an opposite second end, an inside, and an outside;

a head connectable to the body and containing bristles thereon;

a switch electrically connected to a control circuit and being movable between an on position which is actuated and an off position which is de-actuated;

a motor connected to the head for driving the head and electrically connected to the switch for actuation of the motor and moving the bristles when the switch is in the on position and de-actuation of the motor and stopping movement of the bristles when the switch is in the off position;

the control circuit providing a count of the number of uses of the toothbrush by counting the number of actuations of the motor or the number of de-actuations of the motor; and a first display electrically connected to the control circuit displaying a numeric representation of the number of actuations of the motor or the number of de-actuations of the motor, the first display being on the outside of the toothbrush body such that the first display being visible from the outside of the toothbrush body.

4. The toothbrush of claim 3 wherein the first display shows after a predetermined number of uses a message indicating that the head requires replacement.

* * * * *

UNITED STATES PATENT AND TRADEMARK OFFICE
CERTIFICATE OF CORRECTION

PATENT NO.         : 7,596,827 B1
APPLICATION NO.    : 10/985231
DATED              : October 6, 2009
INVENTOR(S)        : Puneet Nanda It is certified that error appears in the above-identified patent and that said Letters Patent is hereby corrected as shown below:

Title Page, Col. 1, Beneath UNITED STATES PATENT:
Item (12) DELETE "Puneet"
Item (12) ADD --Nanda--

Title Page, Col. 1, Line 3:
Item (75) DELETE after Inventor: "Nanda Puneet"
Item (75) ADD after Inventor: --Puneet Nanda--

Signed and Sealed this

Fifteenth Day of December, 2009

David J. Kappos
*Director of the United States Patent and Trademark Office*

UNITED STATES PATENT AND TRADEMARK OFFICE
CERTIFICATE OF CORRECTION

PATENT NO.       : 7,596,827 B1                                      Page 1 of 1
APPLICATION NO.  : 10/985231
DATED            : October 6, 2009
INVENTOR(S)      : Puneet Nanda It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1021 days.

Signed and Sealed this

Twenty-eighth Day of September, 2010

David J. Kappos
*Director of the United States Patent and Trademark Office*